United States Patent [19]

Bush

[11] Patent Number: 4,749,555

[45] Date of Patent: Jun. 7, 1988

[54] PROCESS FOR THE SELECTIVE REMOVAL OF HYDROGEN SULPHIDE AND CARBONYL SULFIDE FROM LIGHT HYDROCARBON GASES CONTAINING CARBON DIOXIDE

[75] Inventor: Warren V. Bush, Houston, Tex.

[73] Assignee: Shell Oil Company, Houston, Tex.

[21] Appl. No.: 914,400

[22] Filed: Oct. 2, 1986

[51] Int. Cl.$^4$ .............................................. C01B 17/16
[52] U.S. Cl. .................................... 423/228; 423/226; 423/243; 423/437; 55/68; 55/73
[58] Field of Search .............. 423/220, 226, 228, 229, 423/232, 243, 437; 55/73, 68

[56] References Cited

U.S. PATENT DOCUMENTS

| | | | |
|---|---|---|---|
| 2,726,992 | 12/1955 | Easthagen et al. | 196/32 |
| 3,965,244 | 6/1976 | Sykes, Jr. | 423/228 |
| 3,989,811 | 11/1976 | Hill | 423/573 |
| 4,163,695 | 8/1979 | Archerd | 203/18 |
| 4,397,660 | 8/1983 | Van der Pas-Toornstra | 55/48 |
| 4,405,582 | 9/1983 | Stogryn et al. | 423/226 |
| 4,412,977 | 11/1983 | Fisch | 423/226 |
| 4,482,529 | 11/1984 | Chen et al. | 423/243 |
| 4,504,449 | 3/1985 | Doerges et al. | 423/228 |
| 4,524,050 | 6/1985 | Chen et al. | 423/243 |
| 4,532,116 | 7/1985 | Doerges et al. | 423/226 |
| 4,539,189 | 9/1985 | Starkston et al. | 423/220 |
| 4,647,397 | 3/1987 | Starkston et al. | 423/220 |

Primary Examiner—Helen M. S. Sneed
Assistant Examiner—Anthony McFarlane
Attorney, Agent, or Firm—Kimbley L. Muller

[57] ABSTRACT

The invention here disclosed is a process for the selective removal of $H_2S$ and COS from a gas stream having a relatively large concentration of $CO_2$ and being predominantly formed of light hydrocarbons, such as methane. This process provides for the selective solvent extraction of $H_2S$ and COS without absorbing $CO_2$. In this process, the solvent comprises a bridgehead amine, a tertiary amine, water, and optionally a physical solvent acceptable to COS absorption, such as sulfolane. The absorption conditions of this process comprise a pressure of from about atmospheric to about 1200 psig and a temperature of from about 40° F. to about 250° F. The treated stream derived from this process contains $CO_2$ and light hydrocarbons and a near absence of $H_2S$ and COS.

16 Claims, 1 Drawing Sheet

PROCESS FOR THE SELECTIVE REMOVAL OF HYDROGEN SULPHIDE AND CARBONYL SULFIDE FROM LIGHT HYDROCARBON GASES CONTAINING CARBON DIOXIDE

FIELD OF INVENTION

The field of this invention relates to the selective removal of $H_2S$ and COS from a gaseous light hydrocarbon stream containing $CO_2$. Sour natural gas that contains an appreciable concentration of $CO_2$, for example greater than 5 to 10%, often contains significant amounts of COS. Even the complete removal of $H_2S$, without the removal of COS, produces a gas which is harmful to downstream processing hardware because the residual COS is converted downstream by hydrolysis to $CO_2$ and $H_2S$, the latter of which then performs its nefarious corrosive activities. A process is sought to provide for the selective absorption of $H_2S$, in addition to COS, but without the absorption of $CO_2$.

In a number of conventional hydrocarbon processing techniques, it is desirable to remove or convert $H_2S$ and COS before contact with any catalytic composition of matter. However, in many cases it is neither necessary nor desirable that carbon dioxide be removed from a gaseous mixture. This is especially true in such areas as coal gasification, where coal is gasified to a syngas and then the resultant vapors treated for $H_2S$ removal before being processed into hydrocarbon components to increase the relative worth of the hydrocarbons.

Sour gas derived from certain natural gas reservoirs is known to contain up to 0.1% by volume COS in addition to large quantities of $H_2S$ and $CO_2$. In order to meet specifications for pipe line transmission it is necessary to remove nearly all of the $H_2S$ and COS, but not necessarily all of the $CO_2$ from the gas. In cases where a Claus plant is utilized to recover sulfur from the acidic components of a gaseous stream, it is advantageous to selectively remove the sulfur-containing acid gas components from the gas mixture while leaving a substantial portion of the $CO_2$ in the treated gas stream since $CO_2$ will act as a diluent in the Claus reactant gases.

BACKGROUND OF THE INVENTION

Aqueous solutions of amines, such as diethanolamine or diisopropanolamine and sometimes containing physical solvents such as sulfolane, have been utilized to treat acid gas streams to remove unwanted components. This type of solvent absorption system is usually not "selective", in that $CO_2$ is absorbed along with the sulfur-containing components, $H_2S$ and COS, with correspondingly increased processing cost. Some aqueous amines, such as methyldiethanolamine (MDEA), with or without the addition of a physical solvent such as sulfolane, will selectively remove $H_2S$ and yet permit $CO_2$ to remain in the treated gas. The problem with this type of solvent absorption is that COS remains in the treated gas with the $CO_2$. It is desirable and beneficial to arrive at a kinetic process for the selective removal of both COS and $H_2S$ while permitting $CO_2$ to remain in the gaseous stream.

Various patentees have attempted such processes but have not yet found a way to accomplish all of the desired process advantages in a relatively simple manner. In U.S. Pat. Nos. 4,524,050 and 4,482,529 (Chen et al), a process is disclosed for the catalytic hydrolysis of COS contained in acid gas streams. The patentees indicate that either a bicyclo tertiary amine ("bridgehead amine") or a bicyclo amidine can be utilized as a catalyst to hydrolyze COS to $H_2S$ and $CO_2$ and thereby eliminate COS as a noxious component from the gas stream. Other catalysts such as platinum on alumina, have been employed for the hydrolysis of COS, but such catalysts have problems of incomplete reaction, and they are limited by the equilibrium of the reaction if the product $H_2S$ and $CO_2$ are not immediately removed from the process environment. Also, monocyclic amines, such as 1,2-dimethylimidazole, have been utilized for the conversion of COS to $H_2S$ and $CO_2$. These disclosures, however, fail to combine the advantageous bicyclo amine or bicyclo amidine and a tertiary amine (not having substituents interconnected) to accomplish their respective absorptive and catalytic functions during acid gas treatment.

In U.S. Pat. No. 3,989,811 (Hill), a process is described for the treatment of sour gas streams containing significant quantities of $H_2S$, $CO_2$ and COS, all of which are absorbed from the gas stream. Suitable solvents are disclosed as aqueous alkali metal carbonates and phosphate solutions, alkanol amines and sulfolanes. This disclosure lacks any appreciation of the use of a tertiary amine or a bridgehead amine for the purpose of selective removal of $H_2S$ and COS without absorption of $CO_2$. U.S. Pat. No. 4,397,660, Van der Pas-Toornstra, discloses a process for the removal of $H_2S$ and $CO_2$ from a gas mixture utilizing a tertiary amine and a physical absorbent such as Sulfinol. This is also a disclosure of a process which will eliminate $CO_2$ from the acid gas stream in addition to $H_2S$ and COS. As exemplary of how difficult it is to remove COS, without also removing $CO_2$, U.S. Pat. No. 4,412,977, Fisch, discloses a process which desires to reduce the sulfur content of a gaseous mixture containing significant quantities of COS in addition to $H_2S$ and $CO_2$. As a result of this process, four separate gaseous streams are produced comprising a purified acid gas-free stream, a COS stream, an $H_2S$ stream and a $CO_2$ stream. Again, this process is selective to $CO_2$ extraction in addition to the removal of $H_2S$ and COS and fails to hydrolyze the COS to other components for their absorption in a tertiary amine.

A process for desulphurizing gases with an amine containing absorbent solution is disclosed in U.S. Pat. No. 4,532,116, Doerges et al. This process has as its objective the preparation of an extremely pure treated gas stream having no more than 3 ppm volume or more total sulphur compounds in the effluent gas. The particular amines chosen to perform this difficult task of removing COS in the presence of $CO_2$ are secondary amines as are exemplified at Column 3 therein. In the instant process, secondary amines are neither desired nor required. The tertiary amines of this invention and the bridgehead amines are not disclosed or taught in this disclosure. In fact, all of the amines used by the patentees are very volatile to enhance condensation during downstream scrubbing. This requires a significant expenditure in energy and results in an economic loss to the process in order to prevent physical loss of the volatile amines. Another U.S. patent by Doerges et al, No. 4,504,499, describes a complex scheme utilizing similar secondary amines. The amines are selective for the removal of COS in the presence of $CO_2$. However, it is necessary to regenerate the amines by a complex scheme, the object of which is to produce a pure $CO_2$ stream, which can be discharged to the atmosphere without further treatment. Also, a rich $H_2S$ stream is desired so that it may be fed directly to a Claus plant for production of sulphur. Another process utilizing secondary amines to absorb COS, and known to absorb nearly all of the $CO_2$, is described in Archerd, U.S. Pat. No. 4,136,695.

In U.S. Pat. No. 3,965,244 (Sykes) a process is described for the selective removal of COS from a gas stream that contains $H_2S$ and $CO_2$. COS is selectively absorbed into a Sulfinol-D solution that is saturated with $H_2S$ and $CO_2$ and contains a high concentration of sulfolane to assist in COS absorption. The absorbed COS is hydrolyzed to $H_2S$ and $CO_2$, which are then returned to a gas phase. In the second step, $H_2S$ is selectively removed from the $CO_2$-containing gas. Thus, a separate step is required to convert the COS to $CO_2$ and $H_2S$. While triethanolamine (TEA) is disclosed in this patent, there is no recognition of the use of a tertiary amine with a bridgehead amine. Finally, in U.S. Pat. No. 2,726,992 (Easthagen et al), a process is described wherein diethanolamine is used for the removal of COS from a liquid petroleum gas. This type of absorption is non-selective and will absorb $CO_2$ even though the same is not mentioned specifically in this disclosure.

A process heretofore has not been described utilizing a conjunct interaction of a bridgehead amine with a tertiary amine in the presence of a physical solvent selective for COS absorption. No hint or suggestion has been provided by these disclosures that the advantageous solvents of the different disclosures can be utilized to arrive at a process whereby COS and $H_2S$ are selectively removed without absorbing $CO_2$.

OBJECTS AND EMBODIMENTS

It is an object of this invention to provide a process to extract and remove $H_2S$ and COS from a gas stream containing a relatively large quantity of $CO_2$ and a predominant quantity of light hydrocarbons to provide: (1) a treated gas stream being relatively free of $H_2S$ and COS and containing a similar large quantity of $CO_2$ and predominant light hydrocarbons, and (2) an acid gas stream containing predominantly $H_2S$ with a minimum concentration of $CO_2$.

Another object of this invention is to provide a process whereby COS can be conjunctly hydrolyzed to $H_2S$ and $CO_2$ and a cosolvent is available to absorb the $H_2S$ but allow the $CO_2$ to pass through with the stream of light boiling hydrocarbon material.

It is another object of this invention to provide a selective process for the removal of COS and $H_2S$ at reaction conditions which include a pressure of from atmospheric pressure to 1200 psig and a temperature of from about 40° F. to about 250° F.

One embodiment of this invention resides in a process for the selective removal of $H_2S$ and COS from a gas stream containing light hydrocarbons and $CO_2$ which comprises contacting said gas stream with a solvent comprising water, a bridgehead amine and a tertiary amine, and if desired a physical solvent suitable for COS absorption, at treating conditions, to selectively absorb said $H_2S$, hydrolyze said COS to $H_2S$ and $CO_2$ and selectively absorb $H_2S$ and to selectively exclude from absorption said light hydrocarbons and $CO_2$.

Another object of this invention resides in a process for the selective removal of COS and $H_2S$ from a $CO_2$-containing stream of predominantly light hydrocarbons by absorption in a solvent comprising: from 0.1 to 5.0 wt% of a bridgehead amine, from 10 to 50 wt% water, from 20 to 60 wt% of a tertiary amine, and from 0 to 40 wt% of a physical solvent selected from the group of sulfolane, propylene carbonate, poly(ethylene oxide) dimethyl ether, and N-methyl pyrrolidone.

Another embodiment of this invention resides in a process for the selective absorption of $H_2S$, and hydrolysis of COS to $H_2S$ and $CO_2$, with selective exclusion of absorption of $CO_2$ from a stream containing $H_2S$, COS, $CO_2$ and light hydrocarbons which comprises treating said stream, at treatment conditions with a solvent comprising water, sulfolane, methyldiethanol amine and a bridgehead amine.

BRIEF DESCRIPTION OF THE INVENTION

This invention concerns a process for the selective removal of $H_2S$ and COS from a gas stream containing light hydrocarbons and $CO_2$ whereby the light hydrocarbons and the $CO_2$ are not affected by the solvent removal and are both present in the treated off-gas. The selective removal is accomplished in the presence of a bridgehead amine, a tertiary amine, and optionally a physical solvent selected from the group of sulfolane, propylene carbonate, (polyethylene oxide)dimethyl ether and N-methyl pyrrolidone.

DETAILED DESCRIPTION OF THE INVENTION

The process here described is for the selective removal of $H_2S$ and COS from a gas stream containing light hydrocarbons and $CO_2$. The particular sour gas stream will contain all three sour gases but the process is selective for the removal of only two gases, $H_2S$ and COS. The sour gas stream may be, for example, a natural gas as derived from a petroleum reservoir, or a refinery gas having these particular components through refining procedures, or a synthesis gas produced by gasification of coal, pitch or a petroleum-derived material. The quantity of the light hydrocarbons will comprise a $C_1$ to $C_4$ hydrocarbon (or CO plus $H_2$ in the case of syngas) and will be the predominant species of the admixture. Preferably, the quantity of light hydrocarbons will be between 50 and 90% of the sour gas stream. The impurities, other than minute impurities, will be a quantity of $H_2S$ equal to 100 ppm to 40 to 50% by weight, a quantity of $CO_2$ of from 100 ppm to 30 to 40 wt%, and COS, from 1 ppm to 0.5 wt%. It is understood that the quantity of the three components, COS, $CO_2$ and $H_2S$, constitute the impurity of the sour gas stream and after their percentage is calculated, which will probably be less than 50%, the remaining or predominant residuum content comprises the light hydrocarbon material.

The process of this invention is carried out in the presence of a unique solvent. The absorption conditions for selectively absorbing $H_2S$ and converting COS to $H_2S$ and $CO_2$ are temperatures of 40° F. to 250° F. and pressures of from about atmospheric pressure to about 1200 psig. It is preferred that the temperature reside between 100° and 120° F. with a pressure of from about 20 psig to 100 psig. The treatment may be performed in either a batch or a continuous type manner, although the continuous type treatment is preferred for economics.

An apparatus useful for this type of process is a continuous flow apparatus in which the absorption solvent will be regenerated and recycled. The use of solvent on a once through basis would require tremendous preparation and disposal resulting in unmanageable volumes of rich and lean solvents. The continuous flow apparatus contemplated by this invention includes a stripper to regenerate solvent for recycle. Ancillary equipment necessary to perform this absorption will comprise coolers and heat exchangers made of steel tubing in order to maintain the flow of rich solvent and lean solvent regenerated to a proper stripping level.

The solvent of this process comprises three components with an option for a fourth: (1) water, (2) a tertiary amine, (3) a bridgehead amine, and (4) a physical solvent acceptable for COS absorption.

The physical solvent acceptable for COS absorption is optional but preferred. It is exemplified by such physical solvents as PEG 400, propylene carbonate, n-beta-hydroxyethylmorpholine, N-methyl pyrrolidone, methanol, sulfolane, tributyl phosphate, (polyethylene oxide)dimethyl ether (also sometimes referred to as Selexol), etc. This component is present in the solvent in a quantity of 0 to 40% (20 to 40 being preferred) based on the total weight of the solvent. Water is present in a weight of from 10 to 60 wt% of the total solvent.

The portion of the solvent which is selective for $H_2S$ absorption but refuses $CO_2$ and COS absorption is a tertiary amine. Tertiary amines have the following formula:

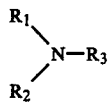

wherein $R_1$, $R_2$ and $R_3$ are not interconnected with one another so as to form a bridgehead and can comprise alkanol moieties of from 1 to 8 carbon atoms, alkyl moities of from 1 to 8 carbon atoms and alkylene oxide oligomers. Preferred type of tertiary amines are alkanol tertiary amines having either the same or different alkanol moieties connected to the nitrogen atom. A specific preferred tertiary amine is triethanol amine or methyl diethanol amine or methyl diisopropanol amine. Specific examples of alkylene oxide oligomers are exemplified by:

$(CH_2-CH_2-O)_nH$, wherein n=1 to 6.

The tertiary amine is present in a quantity of from about 20 to about 60 wt% of the total solution.

More than 0%, i.e. 0.5% but preferably less than 10% and most preferably less than 5% of the solution is comprised of a compound known to enhance COS hydrolysis to $H_2S$ and $CO_2$. It is preferred that the compound be a bridgehead amine comprising bicyclo tertiary amines of the formula:

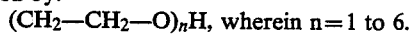

wherein X represents H—C or N; R and R' represent H, $CH_3-$ or $C_2H_5$; R" represents H or $CH_3-$ only if R' is not $C_2H_5$ and m, p and q are equal to or greater than 1. The bridehead amine may also be a bicyclo amidine having the general formula:

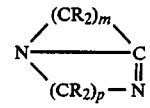

wherein R represents H, $CH_3-$ or $C_2H_5-$, m is 3, 4 or 5 and p is 2, 3 or 4. Specific examples of these types of bridgehead amines and amidines in order of their decreasing order of effectiveness are believed to be:

1,5-diazabicyclo[5.4.0]undec-5-ene ($pK_b$ 1.6)

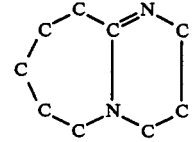

1,5-diazabicyclo[4.3.09 non-5-ene ($pK_b$ 1.3)

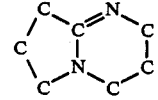

quinuclidine ($pK_b$ 3.5)

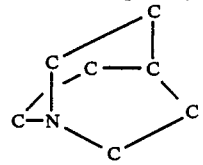

1,4-diazabicyclo[2.2.2]octane ($pK_b$ 5.4)

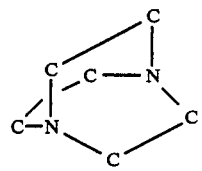

Those bridgehead bases having the lowest $pK_b$'s seem to be the most effective. 1,2-Dimethylimidazole, $pK_b$ 6.3, was essentially inert.

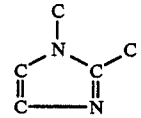

A preferred range of pKb values of the bridgehead amine or bicyclo amidine would be in the range of 0.5 to 5.0.

Conversion of the COS to $H_2S$ and $CO_2$ produces two components, one of which ($H_2S$) is absorbed by the tertiary amine component of the solution, and one of which ($CO_2$) is not readily amenable to absorption by tertiary amines. Thus, the $CO_2$ derived from the COS will pass through along with the light hydrocarbon material and is present as $CO_2$ in downstream processing. The $H_2S$ is removed and eliminated from the sour gas stream.

The above instant species of solvents belong to various genus groups. This invention is to be construed to cover any species within those genus groups which possesses the same or similar selective extraction properties of other members of the denoted genera.

DETAILED DESCRIPTION OF THE DRAWING

Figure 1:
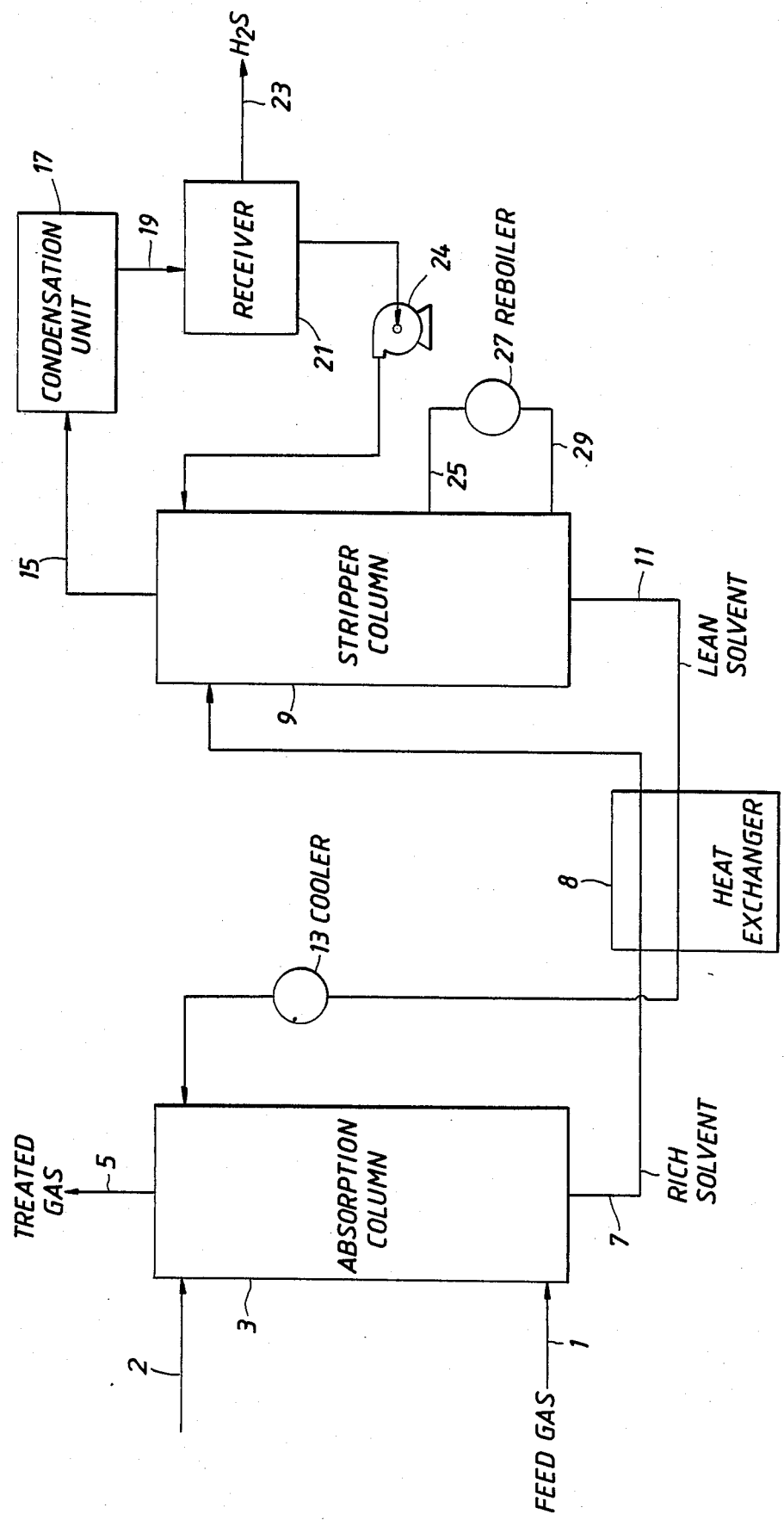
FIG. 1 is a schematic flow scheme of the process of this invention without resort to ancillary equipment such as pumps and valves, the placement of which would be easily ascertainable by one of reasonable skill in the art.

In FIG. 1 a feed gas is charged to a countercurrent absorption column 3 by means of conduit 1. The feed gas is a natural gas derived from a reservoir, a refinery derived gas or syngas having small quantities of COS and either small or large quantities of $CO_2$ and $H_2S$ with the predominant residuum content of the gas being light hydrocarbons or in the case of syngas, a mixture of CO and $H_2$. Countercurrent absorption is performed in absorber 3 at a temperature and a pressure from about 40° F. to about 250° F. and from about atmospheric pressure to about 1200 psig. This countercurrent absorption conjunctly hydrolyzes COS to $H_2S$ and $CO_2$ and absorbs $H_2S$. Fresh or make up absorbent solvent can be added through conduit 2 if necessary to maintain the requisite amount of solvent in the overall absorption system. A treated gas stream is derived in conduit 5 containing the light hydrocarbon and nearly all of the quantity of $CO_2$ added in feed gas 1 and all of the $CO_2$ that is derived from the hydrolysis of COS. This stream also contains substantially none of the $H_2S$ and COS originally present in the feed gas. The upper limit of the quantity of these latter two troublesome compounds in this off-gas stream in conduit 5 will be determined by the use to which the treated gas will be put, but is typically from about 1 ppm $H_2S$ to about 200 ppm $H_2S$ and about 1 ppm COS to about 10 ppm COS. This stream may be processed for further recovery of materials or may be passed to any other type of hydrocarbon processing step. A rich solvent stream is withdrawn from the bottom of absorber 3 in conduit 7 at a temperature of from about 40° F. to about 250° F. and passed with appropriate heat exchange in heat exchanger 8 to stripper column 9 wherein solvent is recovered for passage and return to absorber 3 by means of conduit 11, which again undergoes heat exchange with conduit 7 and heat exchanger 8. It also may be desirable to cool the lean solvent stream in conduit 11 in cooler 13 before passage to countercurrent absorption with the feed gas entered in conduit 1. An acid gas stream is removed from stripper 9 in conduit 15 and passed to a condensation unit 17 wherein the temperature is lowered and a stream is removed in conduit 19 containing the same components but some of which are in liquid phase. In receiver 21 a separation is made of the $H_2S$ gases which may contain a very small amount of $CO_2$ which is removed through conduit 23. Stripper 9 may be reboiled by reboiler 27 and conduits 25 and 29 in the bottom of the stripper. The liquid portion from the separation of $H_2S$ contains a significant quantity of water, and is recycled as reflux to stripper 9 via conduit 22 and pump 24.

The use of this particular solvent system is advantageous for the following reasons:

(1) By means of the proposed process, hydrogen sulfide can be removed selectively from a sour gas that also contains $CO_2$, thereby saving the energy and operating cost for circulating and regenerating the additional volume of solvent that would otherwise be wastefully used in absorbing $CO_2$ as well as $H_2S$.

(2) Carbonyl sulfide can also be selectively removed from a $CO_2$-containing sour gas, also thereby saving energy and operating cost for regenerating the additional volume of conventional solvent that absorbs $CO_2$ along with COS and/or saving the high capital and operating costs associated with the existing, extremely complex combination processes for hydrolysis of COS and subsequent absorption of $H_2S$ and $CO_2$.

(3) A treated gas containing very low concentration of hydrogen sulfide and carbonyl sulfide can be produced, using significantly less solvent circulation than is normally required when using physical solvents such as propylene carbonate or poly(ethylene oxide)dimethyl ether.

(4) An $H_2S$-concentrated gas can be produced from the solvent regenerator (stripper) that contains substantially less $CO_2$ than is produced in conventional amine absorption processes. This results in improved operability and energy generation from the downstream Claus process that is used to convert the recovered $H_2S$ to elemental sulfur.

I claim as my invention:

1. A process for the selective removal of $H_2S$ and COS from a gas containing light hydrocarbons, $H_2S$, COS and $CO_2$, which comprises in a one step absorption, at treatment conditions, contacting said gas stream with a solvent stream consisting essentially of: (i) water, (ii) a bridgehead amine comprising a bicyclo tertiary amine or a bicyclo amidine to selectively hydrolyze said COS to $H_2S$ and $CO_2$, (iii) a tertiary amine to selectively absorb said $H_2S$ and to selectively exclude from absorption said $CO_2$ in said gas stream and said $CO_2$ produced by said hydrolysis of said COS, and (iv) a physical solvent acceptable for COS absorption wherein two streams are formed comprising: (1) a light hydrocarbon and $CO_2$-containing stream having 1 ppm to about 200 ppm $H_2S$ and having 1 ppm COS to about 10 ppm COS and (2) a solvent stream rich in $H_2S$, water, tertiary amine and said bridgehead amine.

2. The process of claim 1 wherein said light hydrocarbons comprise a gas stream containing predominantly $CH_4$ or a light refinery gas having light hydrocarbon gases, at room temperature, selected from methane, ethane, propane and butane.

3. The process of claim 1 wherein said gas stream comprises syngas derived from the gasification of coal or a petroleum derivative.

4. The process of claim 1 wherein said physical solvent acceptable for COS absorption comprises a solvent selected from the group consisting of sulfolane, propylene carbonate, poly(ethylene oxide), dimethyl ether, and N-methylpyrrolidone.

5. The process of claim 1 wherein said tertiary amine comprises an amine of the following structure:

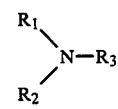

wherein $R_1$, $R_2$ and $R_3$ are individually chosen from alkanol moieties, alkyl moieties and alkylene oxide oligomers.

6. The process of claim 5 wherein said alkanol moieties and alkyl moieties possess between 1 and 8 carbon atoms.

7. The process of claim 6 wherein said tertiary amine is selected from the group comprising methyldiethanol amine and methyl diisopropanol amine.

8. The process of claim 1 wherein said bicyclo tertiary amines have the formula:

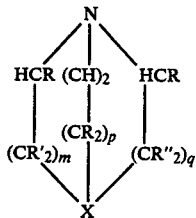

wherein X represents H—C or N, R and R' represents hydrogen, $CH_3$— or $C_2H_5$ and R" represents H or $CH_3$— only if R is not $C_2H_5$— and m, p and q are equal to or greater than 1, and said bicyclo amidines have the formula:

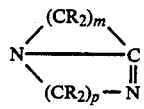

wherein R represents hydrogen, $CH_3$— or $C_2H_5$—, m is 3, 4 or 5 and p is 2, 3 or 4.

9. The process of claim 1 wherein said treatment conditions include a pressure of from about atmospheric to about 1200 psig and a temperature of from about 40° F., to about 250° F.

10. A process for the selective removal of COS and $H_2S$ from a $CO_2$-containing feed stream of predominantly light hydrocarbon in a one step absorption, at absorption conditions, in the presence of a solvent consisting essentially of: (i) from about 10 to 60 wt % water, (ii) from about 0.1 to 5.0 wt % of a bridgehead amine comprising a bicyclo tertiary amine or a bicyclo amidine to selectively hydrolyze said COS to $H_2S$ and $CO_2$, (iii) from about 20 to 60 wt % of a tertiary amine to selectively absorb said $H_2S$ and to selectively exclude from absorption said $CO_2$ in said gas stream and said $CO_2$ produced by said hydrolysis of said COS, and (iv) from about 20 to 40 wt % of a physical solvent selected from the group consisting of sulfolane, propylene carbonate, poly(ethylene oxide)dimethyl ether and N-methyl-pyrrolidine wherein two streams are formed comprising: (1) a light hydrocarbon and $CO_2$-containing stream having 1 ppm to about 200 ppm $H_2S$ and having 1 ppm to about 10 ppm COS and (2) a solvent stream rich in $H_2S$, water, tertiary amine and said bridgehead amine.

11. The process of claim 10 further characterized in that said a bicyclo tertiary amine has the general formula:

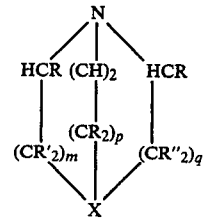

wherein X represents H—C or N; R and R' represent $HCH_3$— or $C_2H_5$—; R" represents H or $CH_3$— only if R' is not $C_2H_5$; and m, p and q are equal to or greater than 1 and bicyclo amidines having the general structure:

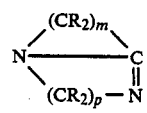

wherein R represents H, $CH_3$— or $C_2H_5$—, m is 3, 4 or 5 and p is 2, 3 and 4.

12. The process of claim 10 wherein said tertiary amine has the structure:

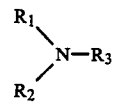

wherein $R_1$, $R_2$, and $R_3$ are equal to an alkanol moiety of from 1 to 8 carbon atoms, an alkyl moiety of from 1 to 8 carbon atoms or alkylene oxide oligomers.

13. The process of claim 10 wherein said selective removal of COS and $H_2S$ are conducted at treatment conditions including a pressure of from about 14 psia to about 1200 psig and a temperature of from about 40° F. to about 250° F.

14. The process of claim 10 wherein said $CO_2$-containing feed stream of predominantly light hydrocarbons comprises from about 1 ppm to 5,000 ppm COS, from 100 ppm to 40% $CO_2$, 100 ppm to 50% $H_2S$ with the residuum of said gas stream comprising light hydrocarbons selected from the group consisting of methane, ethane, propane and butane.

15. The process of claim 10 wherein said $CO_2$-containing stream of predominantly light hydrocarbons comprises a syngas derived from the gasification of coal or a petroleum distillate.

16. The process of claim 10 wherein said tertiary amine comprises methyldiethanol amine and said physical solvent comprises sulfolane.

* * * * *